(12) United States Patent
Ko

(10) Patent No.: US 10,399,005 B2
(45) Date of Patent: *Sep. 3, 2019

(54) SYSTEM FOR STAGED CONTINUOUS COOLED FILTRATION

(71) Applicant: Nextleaf Solutions Ltd., Coquitlam (CA)

(72) Inventor: Ryan Delmoral Ko, Coquitlam (CA)

(73) Assignee: Nextleaf Solutions Ltd., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/291,705

(22) Filed: Mar. 4, 2019

(65) Prior Publication Data

US 2019/0192992 A1    Jun. 27, 2019

Related U.S. Application Data

(63) Continuation of application No. 15/809,980, filed on Nov. 10, 2017, now Pat. No. 10,245,525.

(51) Int. Cl.
*B01D 11/02* (2006.01)
*B01D 46/00* (2006.01)
(Continued)

(52) U.S. Cl.
CPC .......... *B01D 11/0219* (2013.01); *B01D 11/02* (2013.01); *B01D 11/0207* (2013.01); *B01D 11/0284* (2013.01); *B01D 11/0288* (2013.01); *B01D 11/0296* (2013.01); *B01D 11/0492* (2013.01); *B01D 24/007* (2013.01); *B01D 29/56* (2013.01); *B01D 35/18* (2013.01); *B01D 46/0006* (2013.01); *A61K 2236/31* (2013.01); *A61K 2236/333* (2013.01); *A61K 2236/37* (2013.01); *A61K 2236/39* (2013.01); *B01D 2011/007* (2013.01)

(58) Field of Classification Search
None
See application file for complete search history.

(56) References Cited

U.S. PATENT DOCUMENTS 526,695  A  * 10/1894  Emery .................. B01D 39/00
                                                      210/252
2,082,847  A  *  6/1937  Petty ............................. 210/181
(Continued)

OTHER PUBLICATIONS

Patent Cooperation Treaty International Search Report dated Feb. 7, 2019 issued for the co-pending application assigned International Application No. PCT/CA2018/051416 with an International Filing Date of Nov. 8, 2018.

(Continued)

*Primary Examiner* — Robert J Popovics
(74) *Attorney, Agent, or Firm* — Damien G. Loveland

(57) ABSTRACT

A series of vertically oriented filters of decreasing pore size is sealed from the atmosphere. Pressurized gas is used to force the liquid to be filtered through the filters. The filter stages are thermally insulated from ambient temperatures in order to maintain the liquid passing through at a reduced temperature. Each filter stage has a removable lid, which provides convenient access for replacing the filter cartridge, allowing it to be changed without disturbing the thermally insulated sidewalls of the filter stage.

21 Claims, 3 Drawing Sheets

US 10,399,005 B2

Page 2

(51) Int. Cl.
*B01D 11/04* (2006.01)
*B01D 35/18* (2006.01)
*B01D 24/00* (2006.01)
*B01D 29/56* (2006.01)
*B01D 11/00* (2006.01)

(56) References Cited

U.S. PATENT DOCUMENTS

| | | | | |
|---|---|---|---|---|
| 2,121,208 A * | 6/1938 | Milligan | C05B 1/04 | 159/25.2 |
| 2,168,306 A * | 8/1939 | Schutte | C10G 73/06 | 137/13 |
| 2,190,589 A * | 2/1940 | Clayton | C11B 3/06 | 554/199 |
| 2,234,916 A * | 3/1941 | Jones | C10G 73/06 | 208/30 |
| 2,309,633 A * | 2/1943 | Du Pont | C10G 17/10 | 208/13 |
| 2,325,320 A * | 7/1943 | Holuba | C07B 61/00 | 165/101 |
| 2,325,635 A * | 7/1943 | Schutte | C10G 73/025 | 208/29 |
| 2,380,078 A * | 7/1945 | Schutte | C10G 73/06 | 208/29 |
| 2,534,210 A * | 12/1950 | Schutte | B04B 15/06 | 208/28 |
| 2,552,525 A * | 5/1951 | Wenzelberger | A23L 2/12 | 23/296 |
| 2,614,110 A * | 10/1952 | Davis | C11B 1/00 | 210/201 |
| 3,067,067 A * | 12/1962 | Etheridge | C08B 30/20 | 127/71 |
| 3,072,490 A * | 1/1963 | Sargeant | A23L 2/10 | 159/3 |
| 3,254,070 A * | 5/1966 | Roelen | B01J 8/10 | 422/131 |
| 3,270,437 A * | 9/1966 | Lara | B01D 11/0223 | 34/168 |
| 3,555,074 A * | 1/1971 | DuBois | A01N 45/00 | 560/116 |
| 3,817,923 A * | 6/1974 | Ivanov | B01J 19/245 | 526/66 |
| 3,968,741 A * | 7/1976 | Hunt | A47J 37/1223 | 99/330 |
| 4,171,265 A * | 10/1979 | Battigelli | C02F 1/025 | 165/66 |
| 4,279,824 A * | 7/1981 | McKinney | C07D 311/78 | 422/164 |
| 4,784,768 A * | 11/1988 | Mathieu | A61M 1/3462 | 210/321.8 |
| 5,043,100 A * | 8/1991 | Chang | A23L 3/3472 | 252/398 |
| 5,207,929 A * | 5/1993 | Sung | B01D 1/0094 | 210/774 |
| 5,324,867 A * | 6/1994 | Asaoka | C07C 37/70 | 568/723 |
| 5,371,304 A * | 12/1994 | Asaoka | C07C 37/70 | 568/722 |
| 5,382,711 A * | 1/1995 | Asaoka | C07C 37/70 | 568/722 |
| 5,382,712 A * | 1/1995 | Asaoka | C07C 37/70 | 568/722 |
| 5,403,563 A * | 4/1995 | Crosbie | B01J 19/0053 | 261/93 |
| 5,672,280 A * | 9/1997 | Demopoulos | C02F 1/58 | 210/709 |
| 6,095,153 A * | 8/2000 | Kessler | A24F 47/008 | 131/194 |
| 6,103,516 A * | 8/2000 | Reverso | C11B 1/06 | 127/34 |
| 7,622,140 B2 * | 11/2009 | Whittle | B01D 11/0242 | 424/725 |
| 8,197,691 B2 * | 6/2012 | Kale | C11B 1/10 | 210/634 |
| 8,343,553 B2 * | 1/2013 | Hospodor | B01D 11/0219 | 424/725 |
| 8,497,389 B2 * | 7/2013 | Pottathil | C11C 3/10 | 554/162 |
| 9,034,395 B2 * | 5/2015 | Whittle | B01D 11/0242 | 424/725 |
| 9,155,767 B2 | 10/2015 | Hospodor et al. | | |
| 9,199,960 B2 * | 12/2015 | Ferri | C07D 311/92 | |
| 9,242,189 B2 | 1/2016 | Buese et al. | | |
| 9,327,210 B1 * | 5/2016 | Jones | B01D 11/0219 | |
| 9,358,259 B2 * | 6/2016 | Hospodor | A61K 36/185 | |
| 9,655,937 B2 | 5/2017 | Jones | | |
| 9,669,328 B2 * | 6/2017 | Jones | C11B 1/10 | |
| 9,789,147 B2 * | 10/2017 | Jones | B01D 11/0219 | |
| 9,844,740 B2 * | 12/2017 | Jones | C11B 1/10 | |
| 9,873,623 B2 * | 1/2018 | Hawks | C02F 1/66 | |
| 9,987,567 B1 | 6/2018 | Ko | | |
| 10,159,908 B2 * | 12/2018 | Thomas | B01D 1/14 | |
| 10,189,762 B1 * | 1/2019 | Oroskar | A61K 31/05 | |
| 10,195,159 B2 * | 2/2019 | Whittle | B01D 11/0242 | |
| 10,238,745 B2 * | 3/2019 | Finley | A61K 47/22 | |
| 10,245,525 B1 * | 4/2019 | Ko | B01D 11/02 | |
| 2008/0167486 A1 * | 7/2008 | Parnas | C11C 1/08 | 554/174 |
| 2010/0016615 A1 * | 1/2010 | Nakaya | C07D 301/12 | 549/523 |
| 2010/0119606 A1 * | 5/2010 | Whittle | B01D 11/0242 | 424/484 |
| 2011/0040138 A1 * | 2/2011 | Wilson | A61L 11/00 | 588/317 |
| 2011/0078918 A1 * | 4/2011 | Koura | B01D 1/14 | 34/427 |
| 2011/0097626 A1 * | 4/2011 | Waki | C01B 25/455 | 429/199 |
| 2011/0133120 A1 * | 6/2011 | McGhee | B01D 11/0219 | 252/182.12 |
| 2011/0245523 A1 * | 10/2011 | Pottathil | C11C 3/10 | 554/162 |
| 2012/0263804 A1 * | 10/2012 | Hospodor | B01D 11/0219 | 424/725 |
| 2015/0105569 A1 * | 4/2015 | Emo | C11B 9/025 | 554/20 |
| 2015/0375153 A1 * | 12/2015 | Johnson | B01D 9/0013 | 514/5.9 |
| 2016/0030860 A1 * | 2/2016 | McGhee | B01D 11/0207 | 422/116 |
| 2016/0091226 A1 * | 3/2016 | Buese | B01D 11/0219 | 62/115 |
| 2016/0136541 A1 * | 5/2016 | Jones | B01D 11/0219 | 424/725 |
| 2016/0213722 A1 * | 7/2016 | Jones | B01D 11/0219 | |
| 2016/0250564 A1 * | 9/2016 | Thomas | B01D 1/14 | 554/8 |
| 2016/0279535 A1 * | 9/2016 | Jones | C11B 1/10 | |
| 2017/0002292 A1 * | 1/2017 | Cumings | C11B 7/0075 | |
| 2017/0003264 A1 * | 1/2017 | Adams | G01N 33/2823 | |
| 2017/0043276 A1 * | 2/2017 | Tennant | B01D 11/0296 | |
| 2017/0166601 A1 * | 6/2017 | Myerson | B01D 9/0054 | |
| 2017/0252385 A1 * | 9/2017 | Jones | B01D 11/0219 | |
| 2017/0274298 A1 * | 9/2017 | Jones | C11B 1/10 | |
| 2017/0312327 A1 * | 11/2017 | Jones | C11B 1/04 | |
| 2017/0326472 A1 * | 11/2017 | McGhee | B01D 11/0207 | |
| 2018/0008906 A1 | 1/2018 | Kogon | | |
| 2018/0099017 A1 * | 4/2018 | Jones | B01D 11/0219 | |
| 2018/0265803 A1 * | 9/2018 | Cumings | C11B 7/0075 | |
| 2019/0010421 A1 * | 1/2019 | Emo | C11B 9/025 | |
| 2019/0046998 A1 * | 2/2019 | Stephens | B01D 11/0273 | |
| 2019/0099695 A1 * | 4/2019 | Ko | C07C 37/004 | |
| 2019/0099696 A1 * | 4/2019 | Ko | B01D 3/085 | |
| 2019/0111368 A1 * | 4/2019 | Crippen | B01D 39/18 | |

(56) References Cited

U.S. PATENT DOCUMENTS

2019/0143246 A1\* 5/2019 Ko ........................ B01D 11/028
    422/270
2019/0192992 A1\* 6/2019 Ko ......................... B01D 11/02

OTHER PUBLICATIONS

Patent Cooperation Treaty Written Opinon dated Feb. 7, 2019 issued for the co-pending application assigned International Application No. PCT/CA2018/051416 with an International Filing Date of Nov. 8, 2018.

\* cited by examiner

SYSTEM FOR STAGED CONTINUOUS COOLED FILTRATION

TECHNICAL FIELD

This application relates to filtering. More specifically, it relates to a multi-stage, chilled filter arranged in a closed-loop configuration.

BACKGROUND

Filtering is a necessary step in the process of essential element extraction. Traditionally, the vertically oriented in-line and T-form filter housings that exist require the main body of the housing to be lifted off the base in order to replace the filter cartridge inside.

In legal, adult-use markets, sales of cannabis extracts are growing ten times faster compared to the sales of dried cannabis, and extracts account for over 60% of revenue. With legalization, consumer preferences are shifting from dried cannabis to extracted cannabis products. However, the scent and flavors of cannabis can he undesirable in many infused products because of excess lipids, plant matter and impurities present in currently available extracts.

U.S. Pat. No. 9,155,767 to Hospodor et al, relates to the extraction of medicinal cannabis compounds into an eluate, by separating a portion of medicinal cannabis compounds contained within a portion of eluate at a first extraction target level, to provide enough clean solvent to continue extraction operations. A high efficiency concentrator processes eluate from one or more tanks, creating clean solvent when extraction targets are met or when clean solvent is exhausted. This manages eluate concentration levels and limits the quantity of concentrated medicinal cannabis compounds on site at any moment in time.

U.S. Pat. No. 9,655,937 to Jones discloses extraction devices, methods, and systems. Example devices have a solvent chamber, a plant material chamber, a collection chamber, and a solvent return that create a sealed, closed-cycle extraction and/or solvent purification process. Any extractable plant material can he used in the disclosed devices, methods, and systems although in some examples some form of the cannabis plant is used.

This background information is provided to reveal information believed by the applicant to be of possible relevance to the present invention. No admission is necessarily intended, nor should be construed, that any of the preceding information constitutes prior art against the present invention.

SUMMARY OF INVENTION

The present invention is directed to a system of chilled filters connected in a closed-loop configuration for use in the extraction of essential elements from plant material. When extracting essential elements, the plant material is washed and/or soaked in a solvent such as ethanol to result in a crude oil and ethanol mixture, for example. The system of chilled filters is used to filter the crude oil and solvent mixture to remove particulate matter, and may be used at different stages of the extraction process. In particular, the filter system may be used as part of a process for extracting cannabinoids from cannabis plants, for example for medicinal purposes.

Disclosed herein is a filtration system comprising a solvent vessel, a plurality of filter stages and the same plurality of transfer tubes. Each filter stage has a thermally insulated cylindrical side wall; a lid that is removable from said wall; a replaceable, elongated filter cartridge; a support configured to locate a base of said filter cartridge centrally in the filter stage; an inlet port in the lid located to introduce liquid into the filter cartridge; an inlet port configured for introducing pressurized gas outside of the filter cartridge; and a base with an outlet port that drains fluid from outside the filter cartridge. The solvent vessel has a thermally insulated side wall; an inlet port configured for introducing pressurized gas; and an outlet tube having a first end located at a bottom region of the solvent vessel and a second end located outside the solvent vessel. The transfer tubes are each removably connected at an outlet end thereof to one of the inlet ports in one of the lids of the filter stages; and at an inlet end thereof to either the second end of the outlet tube of the solvent vessel or the outlet port of another of said filter stages such that the solvent vessel and the filter stages are connected in series.

BRIEF DESCRIPTION OF DRAWINGS

The following drawings illustrate embodiments of the invention, which should not be construed as restricting the scope of the invention in any way.

DESCRIPTION

A. Glossary

Cannabinoids are a group of chemicals that act on cannabinoid receptors in the body, numerous of which are found in the cannabis plant. Cannabidiol (CBD) is one of the active cannabinoids found in cannabis and is used for medicinal purposes. Tetrahydrocannabinol (THC) is a psychotropic cannabinoid and is the main psychoactive ingredient of cannabis. THC also has medicinal uses. THCa is the non-psychoactive form of THC.

Crude oil is a term for the description of condensed, non-filtered oil, i.e. oil that is non-winterized and not treated via charcoal, clay and silica. The crude oil contains the essential elements. Winterization refers to the removal of unwanted plant waxes and lipids.

B. Apparatus

Figure 1:
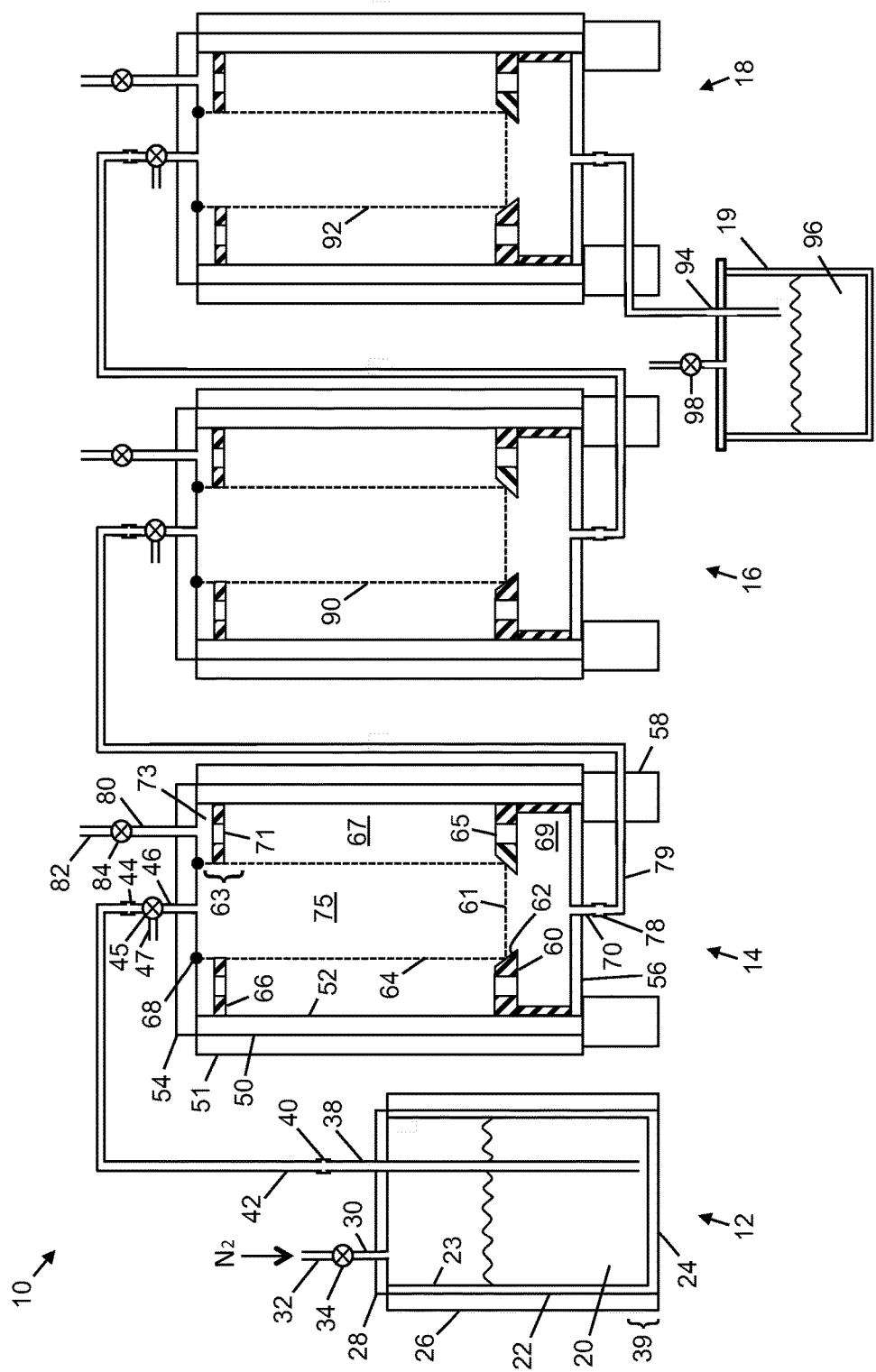
FIG. 1 is a schematic diagram of the closed-loop, multi-stage, chilled filter system, according to an embodiment of the present invention.

Referring to FIG. 1, a closed-loop, multi-stage filter system 10 is shown, which includes a solvent vessel 12, a first filter stage 14, a second filter stage 16 and a third filter stage 18 all connected in series, and a collection vessel 19 for collecting filtered liquids from the system.

The solvent vessel 12 contains the crude oil and solvent mixture 20 that is to be filtered. The crude oil and solvent mixture 20 is the liquid that is drawn out of an extractor column, for example, i.e. after the plant material in the extractor column has been washed and/or soaked with the solvent. The crude oil contains essential elements and is dissolved in the solvent. The mixture also contains some unwanted residual plant matter and other undesirable components. Before the crude oil and solvent mixture 20 is placed in the solvent vessel 12, it may undergo one or more pre-filtering steps. For example, the crude oil and solvent mixture 20 may be pre-filtered with activated charcoal, clay and/or silica. The charcoal removes pigments, chlorophyll, heavy metals and particulates. The clay primarily removes pigments. The silica removes very fine plant matter and other particulates.

The stainless steel solvent vessel 12 has an outer wall 22, an inner wall 23 and a base 24. The outer wall 22 and inner wall 23 form a side wall or jacket that is filled with chilled, pressurized liquid $CO_2$ in order to keep the contents of the solvent vessel 12 cool. Thermal insulation 26 is wrapped around the outer wall 22 of the filter stage 12. In other embodiments, the jacket could be evacuated to provide thermal insulation, and the thermal insulation is not necessary. The main requirement is that the inner wall 23 of the solvent vessel be thermally insulated from ambient temperatures of the surrounding atmosphere in order to keep the contents of the vessel cool. Optionally, the jacket includes the base 24 of the solvent vessel 12, and the base may be further thermally insulated.

A removable lid 28 seals to the top of the solvent vessel 12 so that the contents of the vessel can be pressurized via inlet port 30. Nitrogen gas under pressure is fed into the vessel 12 via inlet tube 32 and valve 34. As the solvent vessel 12 is pressurized, the crude oil and solvent mixture 20 within it is forced out of the vessel through exit tube 38, which forms an airtight seal around its outside with the lid 28. The exit tube has an inlet in the bottom region 39 of the solvent vessel 12 so that liquid in the solvent vessel can readily enter it.

The exit tube 38 is connected via an airtight connector 40 outside of the solvent vessel 12 to a transfer tube 42. The transfer tube 42 is connected in turn via an airtight connector 44 and 3-way valve 45 to the inlet port 46 of the first filtering stage 14. Optionally, the transfer tube 42 is thermally insulated. Additional solvent may be introduced via the inlet tube 47 connected to the 3-way valve 45.

The first filter stage 14 has an outer side wall 50 surrounded by a thermal insulator 51, an inner side wall 52 spaced apart from the outer side wall, a lid 54 that seals to the top of the filter stage and a base 56. The outer wall 50 and inner wall 52 form a side wall or jacket that is filled with chilled, pressurized liquid $CO_2$ in order to keep the contents of the filter stage 14 cool. While different configurations of thermal insulation are possible, the main requirement is that the inner wall 52 of the filter stage 14 is thermally insulated from ambient temperatures in order to keep the contents of the stage cool. Optionally, the jacket includes the base 56 of the filter stage 14, and the base may be further thermally insulated. The first stage 14 is sealed against the atmosphere so that it can be pressurized. The first stage 14 is mounted on supports 58.

A support 60, which is positioned in the bottom of the filter stage 14, has a locating feature such as a beveled edge 62. The locating feature 62 serves to position the lower portion or base 61 of a replaceable cylindrical filter cartridge 64 centrally in the filter stage 14. In other embodiments, different shapes of the support are possible. In this embodiment, the filter cartridge is a polypropylene filter with a pore size in the range of 10-15 μm. Other filter sizes may be used in other embodiments. At the top of the filter stage 14 there is a guide ring 66, which serves to direct the filter cartridge 64 along the axis of the filter stage and maintain an upper portion 63 of the filter cartridge aligned axially within the filter stage. In other embodiments the shape of the guide ring 66 is different.

The support 60 has through holes 65 to permit the passage of filtered liquid from a volume 67 of the filter stage above the support to a volume 69 below it, which is adjacent to and in fluid communication with the outlet port 70. The guide 66 has through holes 71 to permit the passage of filtered liquid from a volume 73 above the guide to the volume 67 below the guide. Supports 60 and guides 66 may have slots or gaps with other shapes to provide fluid communication between the volumes 73, 67, 69 of the solvent vessel. The top of the filter cartridge 64 is sealed to the underside of the lid 54 with an O-ring 68.

The crude oil and solvent mixture 20 enters the filter stage 14 through inlet port 46, which directs the mixture into the inner region 75 of the filter cartridge 64. The mixture is then filtered as it passes out through the side walls and base of the filter cartridge 64. The filtered mixture collects in the bottom of the filter stage 14 and passes out of it through exit port 70 in the base 56 of the filter stage, When required, the cartridge 64 is replaced by disconnecting transfer tube 42 from the lid 54, removing the lid from the filter stage 14, lifting out the cartridge, and then placing a new cartridge in its place. By removing only the lid 54 from the filter stage 14, the side walls 50, 52 can remain in place, together with the thermal insulation 51. This makes it convenient to change the filter cartridge 64, particularly if the filter stage is large. In some embodiments, the side walls 50 can be 1 m tall or more. As well as making the filter cartridge more convenient to change, taller filtration stages can be used within the same headroom compared to stages that require the outer walls to be lifted to change the filter cartridge.

A connector 78 connects a second transfer tube 79 to the outlet port 70 of the filter stage 14. A second port 80 in the lid 54 of the filter stage 14 allows for nitrogen to be supplied directly to the filter stage through tube 82 and valve 84. This is useful in case a blockage occurs upstream in the system 10.

The transfer tube 74 is connected via an airtight connector to the inlet port of the second filtering stage 16. The second filter stage 16 is similar to the first filtering stage 14, except that the filter cartridge 90 has a smaller pore size, which in this embodiment is in the range 3-10 μm. Other filter sizes may be used in other embodiments.

The outlet port at the bottom of the second filter stage 16 is connected via a third transfer tube to an inlet port in the top of the lid of the third filtering stage 18. The third filter stage 18 is similar to the first and second filter stages 14, 16, except that the filter cartridge 92 has an even smaller pore size, which in this embodiment is 1 μm. Other filter sizes may be used in the third filter stage 18 in other embodiments, including filter sizes that are smaller than 1 μm.

The outlet port at the bottom of the third filter stage 18 is connected via a connector and collection pipe 94 to the collection vessel 19, in which the filtered crude oil and solvent mixture 96 is collected. The collection vessel 19 is covered or sealed from the atmosphere with a pressure relief valve 98, although, optionally, it may be uncovered.

A benefit of having the solvent vessel 12 and the three filter stages 14, 16, 18 sealed from the atmosphere is that it reduces the amount of condensation of water into the chilled solvent. This would otherwise dilute the solvent and reduce its effectiveness.

C. Exemplary Process

In use, the crude oil and solvent mixture is chilled either before placing it in the solvent vessel 12 or while it is in the solvent vessel. After this, nitrogen is fed into the solvent vessel 12 at a pressure in the range of about 70-210 kPa (10-30 psi). When the filter system 10 is used for the extraction of essential elements from cannabis and the solvent used is ethanol, the crude oil and solvent mixture is maintained at a temperature between −40° C. and −20° C. in the solvent vessel 12, and remains below −10° C. as it passes through the three filter stages 14, 16, 18.

Figure 2:
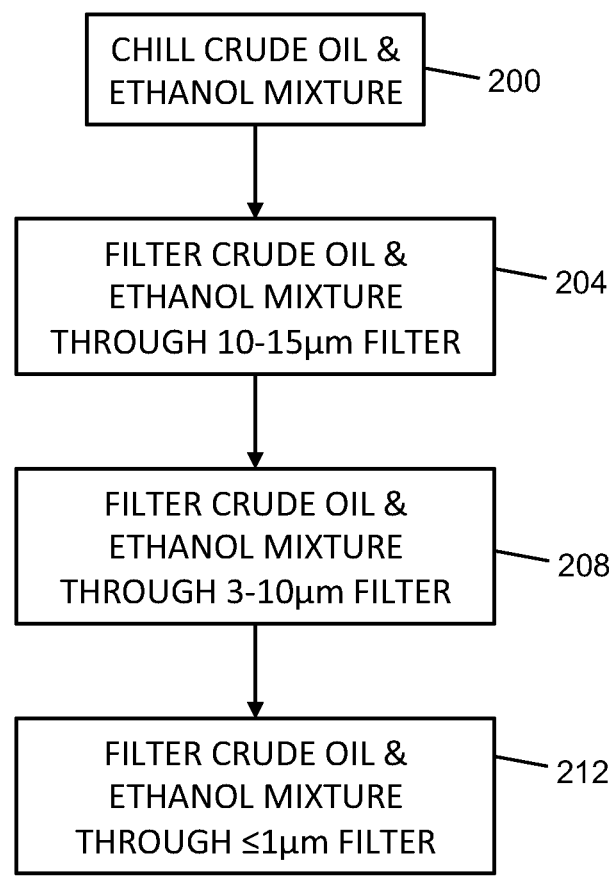
FIG. 2 is a flowchart of a process undertaken using the system of FIG. 1.

Referring to FIG. 2, the first step of the process is to chill the crude oil and ethanol mixture in step 200 to a temperature between −40° C. and −20° C. In step 204, the crude oil and ethanol mixture is filtered through a 10-15 μm filter in the first filtering stage 14. In step 208, the crude oil and ethanol mixture is then filtered through a 3-10 μm filter in the second filtering stage 16. In step 212, the crude oil and ethanol mixture is finally filtered through a ≤1 μm filter in the third filtering stage 18.

D. Variations

While the best presently contemplated mode of carrying out the subject matter disclosed and claimed herein has been described, other modes are also possible.

The outlet tube 38 of the solvent vessel 12 may lead downwards from the base 24 of the solvent vessel, in the same way that the outlet ports 70 are located on the filter stages 14, 16, 18.

Figure 3:
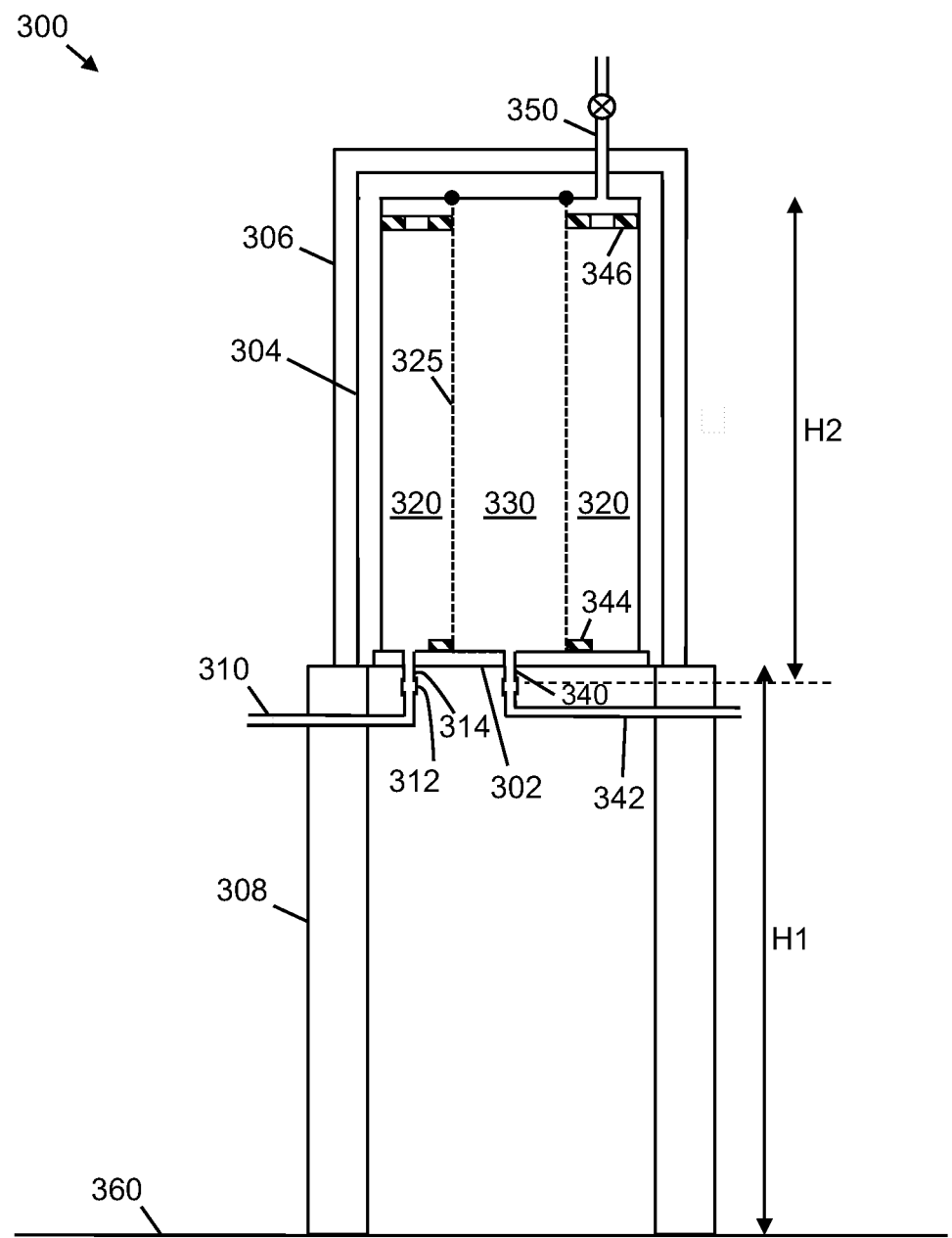
FIG. 3 is a schematic diagram of an alternate embodiment of the closed-loop, multi-stage, chilled filter system of the present invention.

Referring to FIG. 3, an alternate filter stage 300 is shown. Multiple such filter stages can be connected in series as above. The filter stage 300 includes a removable base 302 with jacketed sidewall 304 and surrounding insulation 306, mounted on legs 308 or other equivalent rack or support. An inlet pipe 310 from the previous stage or from the solvent vessel feeds fluid to be filtered into the stage, via the connector 312 and inlet port 314. The fluid to be filtered is fed into the volume 320 to the outside of the filter cartridge 325. As the fluid is filtered, it passes through the cartridge 325 to the volume 330 on the inside of the cartridge, and then leaves the filter stage via outlet port 340 in the removable base 302. Outlet pipe 342 transfers the filtered fluid to the next stage or to the collection vessel 19. The cartridge 325 is aligned with a guide 344 on the removable base 302 and with a spacer 346 at the upper end of the cartridge. A further inlet port 350 is used to introduce nitrogen gas if needed and/or solvent. Other valve and/or inlets may be included in the filter stage 300, e.g. for evacuating the jacket, filling it with chilled liquid $CO_2$, removing fluids from the stage and/or for introducing fluids into the stage.

The legs 308 or other equivalent support holds the body or main sidewall 304 of the filter stage 300 off the floor by a distance that is sufficient to detach the inlet and outlet pipes 310, 342 from the removable base 302, lower the base and remove/replace the cartridge 325 without having to move the sidewall 304 H1. This is possible when distance H1 is greater than distance H2. Distance H1 is the height of the legs off the floor 360 and distance H2 is the height of the cartridge 325 plus the height of the removable base 302 with its permanent fixtures (i.e. inlet port 314 and outlet port 340). It is important not to have to disturb the jacketed sidewall 304 so that the insulation 306 does not need to be moved.

In some embodiments, the apparatus is portable so that it can be taken to the different sites of various plant growers, to be used on an as-needed basis.

Different filter media may be used in this apparatus, such as clay, charcoal and silica.

In other embodiments within the purview of the present invention, other plant materials besides cannabis may be processed. For example, lavender and hemp may be processed, as well as other plants that produce phytochemicals of interest, which include cannabinoids, terpenes, and flavonoids.

Temperatures that have been given to the nearest degree include all temperatures within a range of ±0.5° C. of the given value.

In general, unless otherwise indicated, singular elements may be in the plural and vice versa with no loss of generality.

Throughout the description, specific details have been set forth in order to provide a more thorough understanding of the invention. However, the invention may be practiced without these particulars. In other instances, well known elements have not been shown or described in detail and repetitions of steps and features have been omitted to avoid unnecessarily obscuring the invention. For example, various ports, valves, tubes and other thermal insulation are not shown for clarity. Accordingly, the specification and drawings are to be regarded in an illustrative, rather than a restrictive, sense.

It will be clear to one having skill in the art that further variations to the specific details disclosed herein can be made, resulting in other embodiments that are within the scope of the invention disclosed. All parameters, dimensions, proportions, relative proportions, materials, and configurations described herein are examples only and may be changed depending on the specific embodiment. Accordingly, the scope of the invention is to be construed in accordance with the substance defined by the following claims.

The invention claimed is:

1. A filtration system comprising a solvent vessel, a plurality of filter stages and the same plurality of transfer tubes wherein:
   each filter stage has:
      a thermally insulated cylindrical side wall;
      a lid that is removable from said wall;
      a replaceable, elongated filter cartridge;
      a support having a surface that positions a base of said filter cartridge centrally in the filter stage;
      an inlet port in the lid located to introduce liquid into the filter cartridge;
      an inlet port located to introduce pressurized gas into the filter stage outside of the filter cartridge; and
      a base with an outlet port that drains fluid from outside the filter cartridge; the solvent vessel has:
      a thermally insulated side wall;
      an inlet port for introducing pressurized gas; and
      an outlet tube having a first end located at a bottom region of the solvent vessel and a second end located outside the solvent vessel;
   and the transfer tubes are each removably connected:
      at an outlet end thereof to one of the inlet ports in one of the lids of he filter stages; and
      at an inlet end thereof to either the second end of the outlet tube of the solvent vessel or the outlet port of another of said filter stages such that the solvent vessel and the filter stages are connected in series.

2. The filtration system of claim 1 further comprising a guide positioned to locate an upper portion of the filter cartridge centrally in the filter stage.

3. The filtration system of claim 1 further comprising a seal between each filter cartridge and the lid of the corresponding filter stage.

4. The filtration system of claim 1, wherein each support defines a fluid communication path from a volume above the support to a volume adjacent the outlet port.

5. The filtration system of claim 1, wherein each guide defines a fluid communication path from a volume above the guide to a volume below the guide.

6. The filtration system of claim 1, wherein there are three filter stages and:
a first of the filter stages is connected to the solvent vessel and its filter cartridge has a pore size of 10-15 µm;
a second of the filter stages is connected to the first filter stage and its filter cartridge has a pore size of 3-10 µm; and
the third of the filter stages is connected to the second filter stage and its filter cartridge has a pore size of ≤1 µm.

7. The filtration system of claim 1, wherein each filter cartridge is made from polypropylene.

8. The filtration system of claim 1, wherein the solvent vessel has chilled liquid carbon dioxide in its side wall.

9. The filtration system of claim 8, wherein the side wall of the solvent vessel is at a temperature between −20° C. and −40° C.

10. The filtration system of claim 1, wherein each filter stage has chilled liquid carbon dioxide in its side wall.

11. The filtration system of 10, wherein the side walls of the filter stages are at a temperature of ≤−10° C.

12. The filtration system of claim 1, wherein the pressurized gas is nitrogen that is pressurized to 70-210 kPa.

13. The filtration system of claim 1, wherein the filtration system is sealed from an external atmosphere everywhere except at the outlet port of the filter stage that is at an end of the series.

14. The filtration system of claim 13, wherein the outlet port of the filter stage that is at an end of the series discharges into a collection vessel.

15. The filtration system of claim 14, wherein the outlet port of the filter stage that is at the end of the series discharges via a collection tube into the collection vessel.

16. The filtration system of claim 1, wherein:
the outlet port of the filter stage that is at the end of the series discharges via a collection tube into a collection vessel; and
the collection vessel is sealed from an external atmosphere via a pressure relief valve.

17. The filtration system of claim 1, wherein the transfer tubes are thermally insulated.

18. The filtration system of claim 1, wherein the bases of the filter stages and a base of the solvent vessel are thermally insulated from an external atmosphere.

19. The filtration system of claim 1, wherein the side walls of one or both of the filter stages and the solvent vessel are evacuated.

20. The filtration system of claim 1, wherein the bases of the filter stages and a base of the solvent vessel are double walled and are either evacuated or filled with liquid carbon dioxide.

21. The filtration system of claim 1, wherein each filter stage comprises a further inlet located to introduce solvent into the filter cartridge.

* * * * *